(12) United States Patent
Hiraoka et al.

(10) Patent No.: US 7,902,499 B2
(45) Date of Patent: Mar. 8, 2011

(54) IONIZATION METHOD AND APPARATUS USING ELECTROSPRAY

(75) Inventors: Kenzo Hiraoka, Yamanashi (JP); Atsushi Takamizawa, Yamanashi (JP)

(73) Assignee: University of Yamanashi, Yamanashi (JP)

( * ) Notice: Subject to any disclaimer, the term of this patent is extended or adjusted under 35 U.S.C. 154(b) by 308 days.

(21) Appl. No.: 12/259,871

(22) Filed: Oct. 28, 2008

(65) Prior Publication Data

US 2009/0140137 A1 Jun. 4, 2009

Related U.S. Application Data

(63) Continuation-in-part of application No. PCT/JP2007/059438, filed on Apr. 26, 2007.

(30) Foreign Application Priority Data

Apr. 28, 2006 (JP) ................................. 2006-125398
May 15, 2006 (JP) ................................. 2006-135205

(51) Int. Cl.
*B01D 59/44* (2006.01)

(52) U.S. Cl. ..................... 250/282; 250/423 R; 250/424; 250/281

(58) Field of Classification Search .......... 250/281–288, 250/423 F, 423 R, 424, 425
See application file for complete search history.

(56) References Cited

U.S. PATENT DOCUMENTS

| 5,222,396 | A | * | 6/1993 | Takata et al. ................... 73/618 |
| 5,431,055 | A | * | 7/1995 | Takata et al. ................... 73/618 |
| 5,945,678 | A | * | 8/1999 | Yanagisawa ............... 250/423 F |
| 6,551,557 | B1 | | 4/2003 | Rose et al. |
| 2004/0051037 | A1 | | 3/2004 | Taylor et al. |

FOREIGN PATENT DOCUMENTS

| JP | 7-23796 A | 1/1995 |
| JP | 7-198570 | 8/1995 |
| JP | 8-148117 | 6/1996 |
| JP | 9-306417 | 11/1997 |
| JP | 10-112279 | 4/1998 |
| JP | 2004-333343 | 11/2004 |
| WO | WO 02/082073 A2 | 10/2002 |

(Continued)

OTHER PUBLICATIONS

M. Nakamura, et al. "Development of LC/MS Interface by Laser Spray Ionization" *Reports of Yamanashi Prefectural Fuji Industrial Technology Center*. pp. 57-59. 2005.

(Continued)

*Primary Examiner* — Bernard E Souw
(74) *Attorney, Agent, or Firm* — Dickstein Shapiro LLP (57) ABSTRACT

A biological sample can be subjected to measurement, description and ionization of ions is possible under atmospheric pressure without undergoing pretreatment. Imaging having a resolution on the nanometer order can be performed. An STM needle (probe) of an XYZ-axis-drive piezoelectric element is oscillated along the Z axis to contact the sample to a depth on the nanometer order and capture molecules at the needle tip. A pulsed high voltage is applied to the needle, achieving needle electrospray. The sample molecules are then desorbed and ionized, and mass spectrometry is carried out. The needle is swept in the XY directions, oscillation is repeated and an image obtained by molecular imaging of a nanometer area of the biological sample is measured. The probe may be brought into contact with a droplet produced at the tip of a capillary connected to the outlet port of a liquid chromatograph to capture a sample.

20 Claims, 8 Drawing Sheets

FOREIGN PATENT DOCUMENTS

WO    WO 2004/018104 A1    3/2004
WO    WO 2004/034057 A2    4/2004

OTHER PUBLICATIONS

P. Chaurand, et al. "Imaging Mass Spectrometry: A New Tool to Investigate the Spatial Organization of Peptides and Proteins in Mammalian Tissue Sections," *Current Opinion in Chemical Biology*. vol. 6. pp. 676-681. Aug. 30, 2002.

A.F.M. Altelaar, et al. "Direct Molecular Imaging of *Lymnaea stagnalis* Nervous Tissue at Subcellular Spatial Resolution by Mass Spectrometry," *Analytical Chemistry*. vol. 77, No. 3. pp. 735-741. Feb. 1, 2005.

* cited by examiner

IONIZATION METHOD AND APPARATUS USING ELECTROSPRAY

CROSS-REFERENCE TO RELATED ED APPLICATIONS

This application is a continuation-in-part of International Application No. PCT/JP2007/059438, filed Apr. 26, 2007, which claims priority from Japanese Application No. 2006-125398, filed Apr. 28, 2006, and Japanese Application No. 2006-135205, filed May 15, 2006, the entire disclosures of each of which are incorporated by reference herein.

BACKGROUND OF THE INVENTION

1. Field of the Invention

This invention relates generally to an ionization method and apparatus using electrospray. By way of example, the invention relates to an ionization method and apparatus using electrospray in which imaging is possible, and in another example, to an ionization method and apparatus using electrospray in which microfabrication is possible.

2. Description of the Related Art

Broadly speaking, there are two categories of imaging mass spectrometry for dealing with biological samples and industrial products. The first is matrix-assisted laser desorption ionization (MALDI), and the second is secondary ion mass spectrometry (SIMS). These methods are described in the following literature, by way of example: "Imaging mass spectrometry: a new tool to investigate the spatial organization of peptides and proteins in mammalian tissue sections", Current Opinion in Chemical Biology 2002, 6, 676-681, and "Direct molecular imaging of Lymnaea stagnalis nervous tissue at subcellular spatial resolution by mass spectrometry", Anal. Chem. 2005, 77, 735-741.

To mention one example of a method of sample preparation by MALDI, a biological sample is cooled to −18° C. and a 15-μm section of the biological sample is produced as by using a stainless steel blade. The section is placed on an electrically conductive film and the sample is then dried. The sample surface is thinly coated with a matrix to thereby obtain a MALDI sample, the sample is inserted into a vacuum chamber and MALDI is carried out. There is also a method (laser capture microdissection) in which a biological sample is placed upon a polyethylene film and the macromolecular film is heated momentarily by irradiating it with a laser beam from the back side, thereby transferring the cells at the contact interface to the film. Primarily, a 337-nm nitrogen laser is used in the desorption ionization of the sample ions.

It is difficult to reduce the beam diameter of the laser beam to less than several tens of microns with these methods, and since aberration extends over a wide area, the limit on spatial resolution is 50 μm. Further, by using a matrix, which is the most distinctive feature of MALDI, ion detection sensitivity increases markedly. On the other hand, however, spatial resolution is limited since the crystal size of the matrix applied to the sample exceeds 100 μm.

With the SIMS method, a metal ion source ($Ga^+$, $Au^+$, etc.) that approximates a point light source is employed and a spatial resolution of less than a micron is attained. However, the energy of the ions is large (10 to 20 keV), incident ions penetrate into the sample over a depth of several hundred angstroms and the sample sustains damage. Consequently, the yield of ions from a readily decomposed sample such as a biological sample declines rapidly with time. Since the sample desorbed is limited to the molecules in the proximity of the surface, the detection sensitivity of ions with respect to biologically related samples is low.

Cluster SIMS has been developed for the purpose of eliminating this drawback. It has become evident that the desorption efficiency of secondary ions increases sharply if gold cluster ions ($Au_n^+$) or $C_{60}^+$ ions, for example, are used as the incident ions.

However, a spatial resolution of less than a micron is difficult to obtain because the current of the primary ion beam is small and the ion beam diameter is greater than several microns. These SIMS methods are all difficult to apply to high-mass molecules such as biological macromolecules.

Imaging techniques using MALDI or SIMS of the kind described above are continuing to come into widespread use in the field of life science. With these methods, however, it is difficult to obtain a resolution of less than a micron owing to the fundamental limitations thereof. In addition, since the sample must be introduced into the vacuum system of a mass spectrometer that operates only under high vacuum, preliminary treatment is very troublesome. Accordingly, no matter what improvements are applied to the conventional MALDI or SIMS methods, it is nearly impossible to realize a resolution of less than a micron so long as these are adopted as the basic techniques.

A method of mass spectrometry for real-time nanoscale (less than 1 μm) measurement of an imaging image non-destructively while a biological sample or the like is maintained as is under atmospheric pressure has not been developed thus far.

On the other hand, with conventional electrospray or nano-laser spray, a sample liquid forms a conical shape (referred to as a "Taylor cone") at the tip of a capillary and a minute charged droplet is produced from the conical tip. Owing to the viscosity of the liquid, it is fundamentally impossible to impart this droplet with a size of less than a micrometer or submicrometer. The reason for this is that when the tip of the Taylor cone is torn off by the force of the electric field to produce the droplet, the diameter of the tip of the Taylor cone takes on the submicrometer size automatically owing to the viscosity of the liquid. Thus, droplet size capable of being produced by electrospray is decided in the manner of a natural occurrence and it is difficult to achieve a further reduction in size.

Further, with conventional electrospray, achieving the nanometer level (nanoelectrospray) is accompanied by the need to reduce capillary diameter. There are many limitations such as clogging. It is difficult to produce a spray and handling is troublesome. Furthermore, with conventional electrospray, an increase in salt concentration results in spraying difficulty and there is a sudden decline in desorption efficiency of ions into the gaseous phase. Accordingly, conventional electrospray cannot be applied to NaCl aqueous solutions on the order of 150 mM, such as physiological saline solution.

DISCLOSURE OF THE INVENTION

The present invention provides an ionization method and apparatus in which biological tissue and the like without pre-treatment can be adopted as a sample of interest and, moreover, it is possible to desorb and ionize the sample ions under atmospheric pressure.

Further, the present invention provides an ionization method and apparatus in which a miniscule sample can be handled without causing clogging and the like and, moreover, it is possible to produce an electrospray efficiently.

Further, the present invention provides an ionization method and apparatus capable of producing the electrospray phenomenon even with regard to a liquid biological sample and sample having a high salt concentration.

Further, the present invention provides an ionization method and apparatus in which imaging having a resolution on the nanometer (nm) order is possible.

Further, the present invention provides a mass spectrometry method and apparatus using the above-mentioned ionization method and apparatus.

An ionization method using electrospray according to the present invention comprises oscillating a metal probe along the longitudinal direction thereof, with enough amplitude to bring the tip of the probe into contact with a sample, at an origin position where the tip of the probe is in close proximity to the sample; applying a voltage, which produces electrospray, to the probe; and capturing the sample at the tip of the probe and ionizing the sample. The probe is oscillated between the origin position (top end point) and a position (bottom end point or sample capture position) at which the tip of the probe contacts the sample. Sample ions produced under atmospheric pressure are introduced to a mass spectrometer either through an ion-sampling capillary or orifice, or directly. It is assumed that the oscillation is not only periodic motion but also includes motion (movement) in which the probe is reciprocated only one time between the origin position and the sample capture position.

An ionization apparatus according to the present invention comprises sample holding means for holding a sample; a metal probe to which a voltage is applied; and an oscillating device for oscillating the probe along the longitudinal direction thereof. The oscillating device includes a device for reciprocating the probe only once along the longitudinal direction.

In accordance with the present invention, ionization can be performed under atmospheric pressure (in the atmosphere, in another inert gas or in a saturated vapor pressure chamber) without requiring that the metal probe or sample be placed in a vacuum chamber. The sample can be used as is without applying a pre-treatment. It is possible to use a biological sample as the sample.

With probe (needle) electrospray according to the present invention, the probe is oscillated to thereby capture the sample at the tip of the probe and produce the electrospray. Since a probe (needle) is used, clogging does not occur. If a probe having a sharp tip is used, an electrospray can be produced efficiently (the effect of the electric field is enhanced to the limit). Since the probe is oscillated, the amount of sample taken up by the probe can be enlarged; the higher the oscillation frequency is made, the more the amount of sample captured. Furthermore, if a probe (needle) having a tip diameter on the atomic level is used, then a nanometer level for the diameter of the needle tip can be achieved to the maximum degree. As a result, the electrospray phenomenon can be produced even for samples having a high salt concentration. The voltage applied to the probe is applied so as to produce a potential difference between the probe and another member, e.g., a part of the mass spectrometer or a member related thereto (an orifice or skimmer, etc., having an ion sampling hole, or a sampling tube or capillary, etc.), the sample holding means (sample) or a member related thereto (depending upon the case, there are instances where it is desired to so arrange it that almost no potential difference is produced between the probe and sample holding means, although various modes of applied voltage will be described later).

Furthermore, in a preferred embodiment, a laser device for irradiating the vicinity of the probe tip with laser light (ultraviolet, infrared or visible light) is provided, and the vicinity of the probe tip at the origin position or a position somewhat removed from the tip (a spaced-away position beneath the tip) is irradiated with the laser beam.

In the case of visible laser light [e.g., a frequency-doubled (532 nm) YAG laser], a surface plasmon is induced on the metal (probe) surface irradiated with the laser beam. The surface plasmon propagates along the probe surface toward the tip and intensifies the electric field strength in the vicinity of the probe tip. Accordingly, desorption ionization of sample molecules by electrospray is intensified. In a case where use is made of infrared laser light, promotion of sample drying and efficiency of ion desorption from a droplet are improved by heating the sample, which has been captured in the vicinity of the probe tip, and the metal surface. Further, owing to the effect of heating, non-covalent-bonded compounds and the like can be dissociated selectively into individual subunits. With infrared laser irradiation, it is possible to observe the dissociation of a non-covalent-bonded compound, which plays an important role in biological reactions.

In another embodiment of the present invention, a solvent is sprayed toward the vicinity of the probe tip at the origin position. This is effective in a case where the sample dries or, as in a biological sample, component concentration is high and it is difficult to produce the electrospray.

Although the voltage (a comparatively high voltage) that produces the electrospray may be applied to the probe constantly, it is preferred that the voltage for producing the electrospray be applied to the probe in the period of time during which the probe is at the origin position or in the vicinity thereof. Preferably, when the tip of the probe is in contact with the sample or during the time in which it is in the vicinity, the probe potential is made the same as that of the sample or, in order to capture ions from the sample selectively, a comparatively low voltage suited to this purpose is applied.

In an embodiment, the ionization apparatus has a power supply unit for generating a pulsed voltage applied to the probe, the pulsed voltage being such that at least one among amplitude, pulse width and pulse waveform can be varied. It is preferred that the value of the voltage applied to the probe and the duration of application, etc., be adjustable.

In another preferred embodiment, the voltage for producing the electrospray is applied to the probe in a period of time during which the probe tip is in the vicinity of the origin position, and irradiation with the laser beam and application of the voltage are performed simultaneously. That is, the voltage is applied to the probe and irradiation with the laser beam is performed when the probe is at the origin position or in the vicinity thereof.

The probe may be subjected to a temperature adjustment in accordance with the state of the sample in order to so arrange it that more of the sample is captured by the probe. For example, it is possible to control the temperature of the probe by attaching a Peltier element (a temperature adjustment element) to the holder of the probe.

Furthermore, in order to enlarge the amount of sample captured, a mode can be adopted in which the probe is rotated or the tip of the probe is formed to have unevenness to thereby increase the surface area thereof.

In the case of a solid sample that contains liquid, such as a biological sample, the sample should be supplied by placing it on a sample table. The sample may be placed in a vessel.

In the case of a solid sample that contains liquid, such as a biological sample, imaging in particular is possible. That is, if the size of the probe tip is made on the order of nanometers and the minimum unit of amount of displacement when the probe is displaced along the sample surface can be controlled on the nm order, then the sample molecules can be captured by the probe with a resolution on the nm order. Accordingly, it will be possible to measure (to image) the distribution of molecules on the sample surface on the order of nanometers.

An ionization apparatus according to the present invention for implementing the above-described ionization method comprises: a sample table for holding a sample; a metal probe; an oscillating device for oscillating the probe along the longitudinal direction thereof; and a three-dimensional-displacement driving unit for moving at least one of the sample table and probe relatively toward and away from each other and translating the same.

In a preferred embodiment, first an image regarding the sample surface (a height distribution, etc.) is obtained and the location (search area) at which the sample molecules are captured in this image is decided.

A method of implementing this embodiment includes moving the probe in a direction substantially along the sample surface (so as to trace the surface) while holding constant the distance between the probe tip and sample surface; obtaining an image of the sample surface conforming to the position of the probe; specifying a search area on this image; bringing the probe to the origin position within the search area; and oscillating the probe along the longitudinal direction thereof (inclusive of reciprocating the probe one time). The search area may be moved sequentially.

If the sample is taken up not only at the sample surface but also at various positions along the depth direction, then three-dimensional imaging is possible. In particular, in cases where the sample surface is covered with a hard membrane, as in the manner of a cell or the like, it will suffice to pierce the sample, insert the probe into the pierced hole and capture the sample. A probe having a tip in which threads have been cut may be used to pierce the sample.

In a case where the present invention is applied to a liquid sample, the liquid sample may be supplied from the tip of a capillary. In a preferred embodiment, the capillary is an electrospray capillary to which a voltage is applied. The liquid sample may be supplied by being placed in a vessel.

In a preferred embodiment, the probe and the capillary are placed at the same potential (or at a potential difference near the same potential to such an extent that an electrospray or electrical discharge will not occur). Preferably, voltage is applied so as to produce a potential difference, which will produce an electrospray, between the probe and capillary and a part of the mass spectrometer (or a member related thereto) or another member.

In accordance with the above-described method, the invention can be applied as is to a liquid chromatography apparatus. That is, a liquid sample is supplied to the above-described capillary from liquid chromatography.

Thus, the present invention is applicable to a sample with a high salt concentration and to liquid samples, etc., as set forth above.

If platinum or tungsten usable at high temperatures is used as the probe (needle), the probe will not be degraded by the laser light (visible or infrared laser light).

In another aspect of the present invention, an ionization method using electrospray, comprises the steps of: holding a probe so as to be capable of reciprocating between a bottom end point at which a tip of the probe contacts a sample and a top end point at which the tip of the probe is spaced away from the sample; arranging an ion guide introducing sample ions to a mass spectrometry apparatus such that the tip of the ion guide is positioned in the vicinity of the tip of the probe in the vicinity of the top end point; moving the probe toward the bottom end point and bring the tip of the probe into the contact with the sample to capture the sample; causing the probe and the sample to be at the same potential at least during the probe contacts the sample; and subsequently, moving the probe toward the top end point, and applying a high voltage for electrospray between the probe and the ion guide, at least at a time when the probe is separated from the sample, to thereby ionize the sample captured at the tip of the probe. The generated sample ions are introduced into the mass spectrometry apparatus via the ion guide and are subjected to the mass spectrometry.

An ionization apparatus of another aspect of the present invention comprises: holding means for holding a probe so as to be capable of reciprocating between a bottom end point at which a tip of the probe contacts a sample and a top end point at which the tip of the probe is spaced away from the sample; an ion guide, arranged such that the tip of the ion guide is positioned in the vicinity of the tip of the probe in the vicinity of the top end point, for introducing sample ions from the tip thereof to a mass spectrometry apparatus; and a high voltage generating apparatus applying a high voltage for electrospray between the probe and the ion guide, at least at a time when the probe is separated from the sample.

Since the probe and the sample are placed at the same electric potential at least during the probe contacts the sample, it is not necessarily needed to take measures (operation or means) for positively placing the probe and the sample at the same potential (the sample may be placed in an electrically floating state). Of course, the probe and the sample (e.g., a sample stage on which the sample is placed or a capillary supplying a liquid sample) may be electrically coupled so as to forcedly place them at the same potential. The probe is of conductive (e.g. a metal).

A high voltage for electrospray may be applied between the probe and the ion guide at all times during the measurement or analysis (mass spectrometry). This leads a simple high-voltage application control. Of course, a pulsed high voltage may be applied between the probe and the ion guide after the probe is separated from the sample.

In accordance with the present invention, an electrospray is produced from the probe toward the ion guide by an electric field generated by the high voltage applied between the probe and the ion guide, immediately after the probe is separated from the sample (or at a moment when the probe is separated from the sample). In this case, the tip of the probe can be fairly close to the tip of the ion guide (e.g. up to few or several millimeters). The sample ions generated by the electrospray are effectively introduced to the mass spectrometry apparatus.

In one embodiment of the present invention, the vicinity of the tip of the probe at the top end point is irradiated with a laser beam. In another embodiment, a solvent is sprayed toward the vicinity of the tip of the probe at the top end point.

The present invention also provides an ionization method and apparatus that utilizes capture of a sample by a probe oscillated in the above-described ionization method and ionization apparatus, and applies another electrospray method (apparatus) (side electrospray).

This ionization method comprises capturing a sample at the tip of a probe by oscillating the probe along the longitudinal direction thereof [i.e., by oscillating the probe between a top end point and a sample acquisition position (a bottom end point)], with enough amplitude to bring the tip of the probe into contact with the sample, at an origin position where the tip of the probe is in close proximity to the sample; and ionizing the sample by exposing the sample, which has been captured at the tip of the probe, to electrospray in the vicinity of the origin position. Oscillation includes reciprocating the strobe one time between the top end point and the sample capture position.

The ionization apparatus comprises: sample holding means for holding a sample; an oscillating device for oscillating a probe along the longitudinal direction thereof; and an electrospray unit for forming a field of an electrospray at a position in the vicinity of the tip of the probe. The oscillating device may reciprocate the one time.

The sample captured by at the probe tip is wetted and diluted by a charged droplet supplied by electrospray using a suitable solvent, whereby desorption and ionization of the sample are promoted. The ionized sample, as necessary, is introduced to an analyzing apparatus using a pneumatically conveying assist gas.

The probe may an insulator. It may be so arranged that a metal probe is used and a voltage for producing electrospray is applied to the metal probe, and it can be so arranged that the vicinity of the probe tip at the origin position is irradiated with a laser beam.

Furthermore, the present invention further provides an analyzing method and apparatus for mass spectrometry of a sample ionized by all of the above-described ionization methods or ionization apparatuses.

DESCRIPTION OF THE PREFERRED EMBODIMENT

Figure 1:
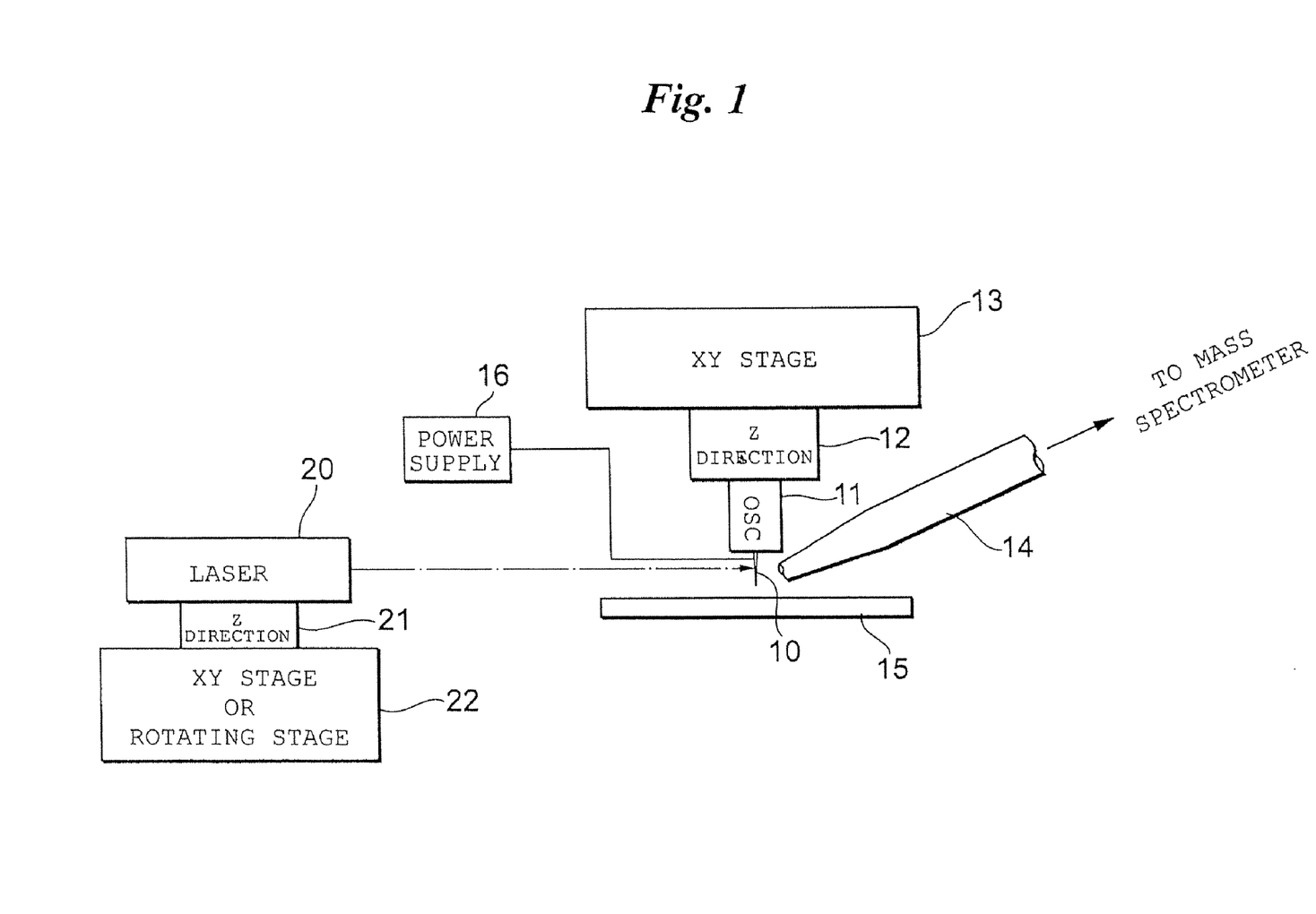
FIG. 1 is a block diagram illustrating the configuration of an ionization apparatus according to a first embodiment.

FIG. 1 illustrates the configuration of an ionization apparatus capable of imaging according to a first embodiment.

This ionization apparatus is capable of operating under atmospheric pressure. Sample ions desorbed and ionized from a sample by this ionization apparatus are introduced to a mass spectrometry apparatus. Although an orthogonal time-of-flight mass spectrometer can be mentioned as an example of the mass spectrometry apparatus, the present invention is also applicable to a mass spectrometry apparatus such as a (linear) ion-trapping mass spectrometry apparatus.

A sample table 15 is secured to the ionization apparatus at a suitable location. A biological sample is placed on the sample table 15 as is (without being subjected to a pre-treatment, as in the case of MALDI). For the sake of convenience, the upper surface of the sample table 15 is adopted as the XY plane and the direction perpendicular thereto is adopted as the Z direction.

An XY stage 13 is placed above the sample table. The XY stage 13 holds a Z stage 12 in a manner movable along the XY direction. A driving source for displacing the XY stage 13 in the X direction and Y direction is one capable of applying mechanical displacement, such as a piezoelectric element or mechanical driving device, by way of example. Preferably, displacement in the X and Y directions can be controlled with a resolution on the nm order.

The Z stage (actuator for height adjustment) 12 holds a Z-direction oscillating device 11 in a manner movable along the Z direction. This also is driven by means having a movement function with good mechanical reproducibility, such as a piezoelectric element, motor driving or magnetic driving device, and preferably the amount of displacement can be controlled on the nm order along the Z direction.

A probe (needle) 10 made of metal is mounted on the oscillating device 11. The tip of the probe 10 has been micromachined to a size on the nm order. The probe 10 is directed perpendicular (along the Z direction) to the sample table 15 and is driven in oscillatory fashion in the Z direction (the longitudinal direction of the probe 10 is perpendicular to the upper surface of the sample table 15). The frequency and amplitude of oscillation and the number of oscillations (inclusive of a single oscillation) by the oscillating device 11 can also be controlled. The oscillating device 11 and Z stage 12 may be combined and implemented by a single Z-direction oscillatory driving device.

A positive or negative voltage (e.g., ±several hundred volts to ±several thousand volts, for which the details will be described later, with the sample table 15, the sample on the sample table 15 or an ion sampling capillary 14 serving as the reference) for electrospray is applied to the probe 10 (preferably between the probe and the ion-sampling capillary 14, described later) by a variable-voltage power supply device 16. A positive voltage is applied in a case where positive ions are obtained and a negative voltage in a case where negative ions are obtained.

Instead of the arrangement in which the probe 10 is displaced in the XY directions and Z direction by the XY stage 13 and Z stage 12, an arrangement may be adopted in which the sample table 15 is displaced in the XY directions and Z direction.

The ionization apparatus is provided with a laser unit 20 (e.g., a YAG laser) the laser emission direction of which is pointed toward the probe 10. The laser unit 20 is supported so as to be freely positionally adjustable in the XY directions and Z direction by an XY stage 22 and Z stage 21. A rotating stage can be used instead of the XY stage.

The tip of the ion-sampling capillary 14 is arranged so as to face the vicinity of the location where the probe 10 is provided. The capillary 14 is for introducing sample ions, which are generated at this location, to a mass spectrometry apparatus.

Figure 2:
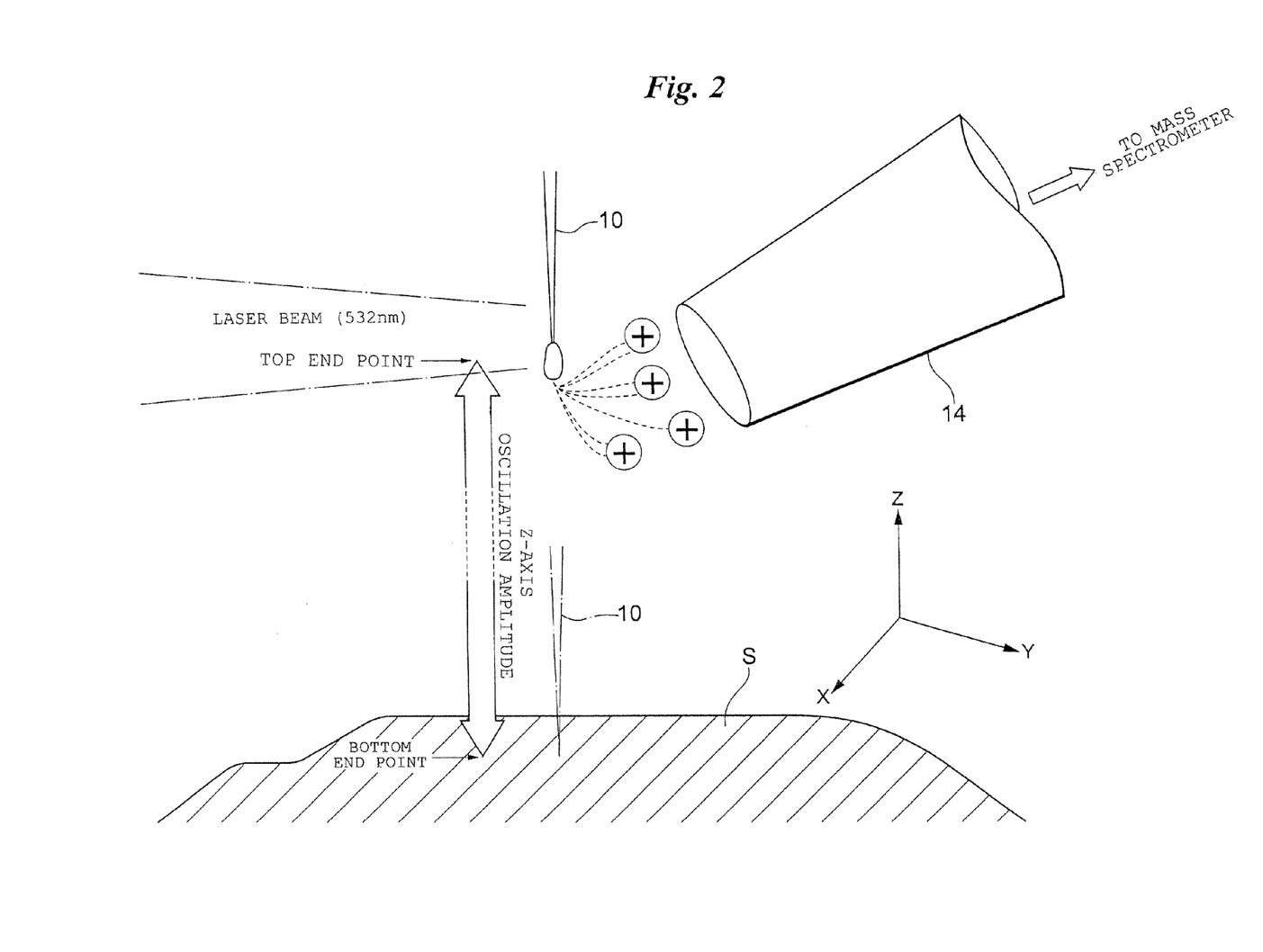
FIG. 2 illustrates the manner in which ionization is performed.

One example of an ionization method using this ionization apparatus will be described with reference to FIG. 2.

The Z stage 12 is driven to make the tip of the probe 10 approach a sample S while the probe 10 is oscillated (displaced) parallel (in the XY directions) to the surface of the sample S, which has been placed on the sample table 15, by the XY stage 13. By approaching the sample surface, the probe 10 sustains a shearing force and a change occurs in the number of oscillations. With the distance between the surface of the sample S and the tip of the probe 10 held fixed by feeding back this change to the Z stage 12 (the height-adjusting actuator), the probe 10 is displaced in the XY directions by the XY stage 13 to thereby obtain an imaging image of the surface of the sample S (the image of positions along the Z direction) at a resolution on the nm order. Next, an area to be searched is specified based upon the imaging image obtained.

At a prescribed position within the specified search area, the tip of the probe 10 is positioned at a position several tens of microns to several millimeters above the sample surface (this position will be referred to as the "origin point" or "top dead center", "top end point" or "upper-limit position", described later). The probe 10 is oscillated downward from the origin position along the Z direction (in the direction toward the sample S) by the oscillating device 11. The amplitude of oscillation is several tens of microns to several millimeters and an adjustment is made such that with the probe 10 at its lowermost position (the sample capture position, bottom dead center, bottom end point or lower-limit position), the tip of the probe will contact the surface of the sample S to a depth on the nm order. It will suffice merely to reciprocate the probe between the top end point and bottom end point once. That is, it is assumed that a single reciprocation of the probe falls within the concept of oscillation. By bringing the tip of the probe 10 into contact with the sample S at the bottom end point, biological molecules in the sample S are taken up on the tip of the probe having a size on the nm order. When the probe 10 is raised and reaches the top end point, a pulsed voltage of several tens to several thousand volts is applied to the probe, as will be described later. An electrospray is produced at the tip of the probe 10 and the sample molecules are desorbed and ionized in the gaseous phase. The sample ions thus generated are drawn in by the capillary 14 and sent to the mass spectrometry apparatus. The above-described operation is performed while position in the XY directions is changed as necessary. It is also permissible to hold position in the XY directions fixed and change the depth (position along the Z direction) to which the probe penetrates into the sample S. In order to raise the sample holding (sampling or capture) efficiency, the needle tip may be subjected to machining to roughen its surface (e.g., the tip of the probe 10 is cut to have grooves such as threads, as will be described later).

The probe 10 at the origin position is irradiated by the laser unit 20 from the side direction with, e.g., YAG laser light (frequency-doubled) having a wavelength of 532 nm. With the probe 10 at the position (origin position) where it has been raised to the uppermost portion, the position is adjusted in such a manner that the irradiation with the laser beam will be performed within several microns from the vicinity of the tip of probe 10. A surface plasmon is induced on the metal (probe 10) surface irradiated with the laser beam. The surface plasmon propagates along the surface of the probe 10 toward the tip and intensifies the electric field strength in the vicinity of the probe tip by several orders of magnitude. Further, in case of irradiation with infrared laser light, the probe surface moistened by the sample is heated rapidly and the desorption of the captured sample is promoted owing to the effect of heating. Further, owing to heating by the infrared laser, it is also possible to observe the selective dissociation of a non-covalent-bonded compound or the like of the biological sample into the subunits. The probe tip is not irradiated directly with the infrared laser beam, but rather the neighborhood spaced away from the probe tip (e.g., slightly below the tip) is irradiated. As a result, a charged droplet sprayed from the probe tip can be heated. Such heating can promote the vaporization of the ions in the charged droplet into the gaseous phase and can strengthen the ion signal.

By thus irradiating the tip of the probe 10 with the 532-nm laser beam, a plasmon is induced and the desorption efficiency of the sample ions is further intensified. The ionization method of this embodiment boosts desorption and ionization to the maximum degree by the technique of combining electrospray and plasmon excitation. Ions that have desorbed into the gaseous phase under atmospheric pressure are conveyed to a time-of-flight mass spectrometer by the ion-sampling capillary 14, and the ions are separated and detected. An image obtained by imaging at a resolution on the nm order can be observed by sweeping the needle in the XY directions. Although a plasmon is difficult to excite with infrared laser irradiation, an increase in ion desorption efficiency and selective dissociation of non-covalent-bonded compounds, etc., can be brought about by the surface heating effect of laser irradiation or by the promotion of vaporization of ions by the heating of the charged droplet.

Figure 3:
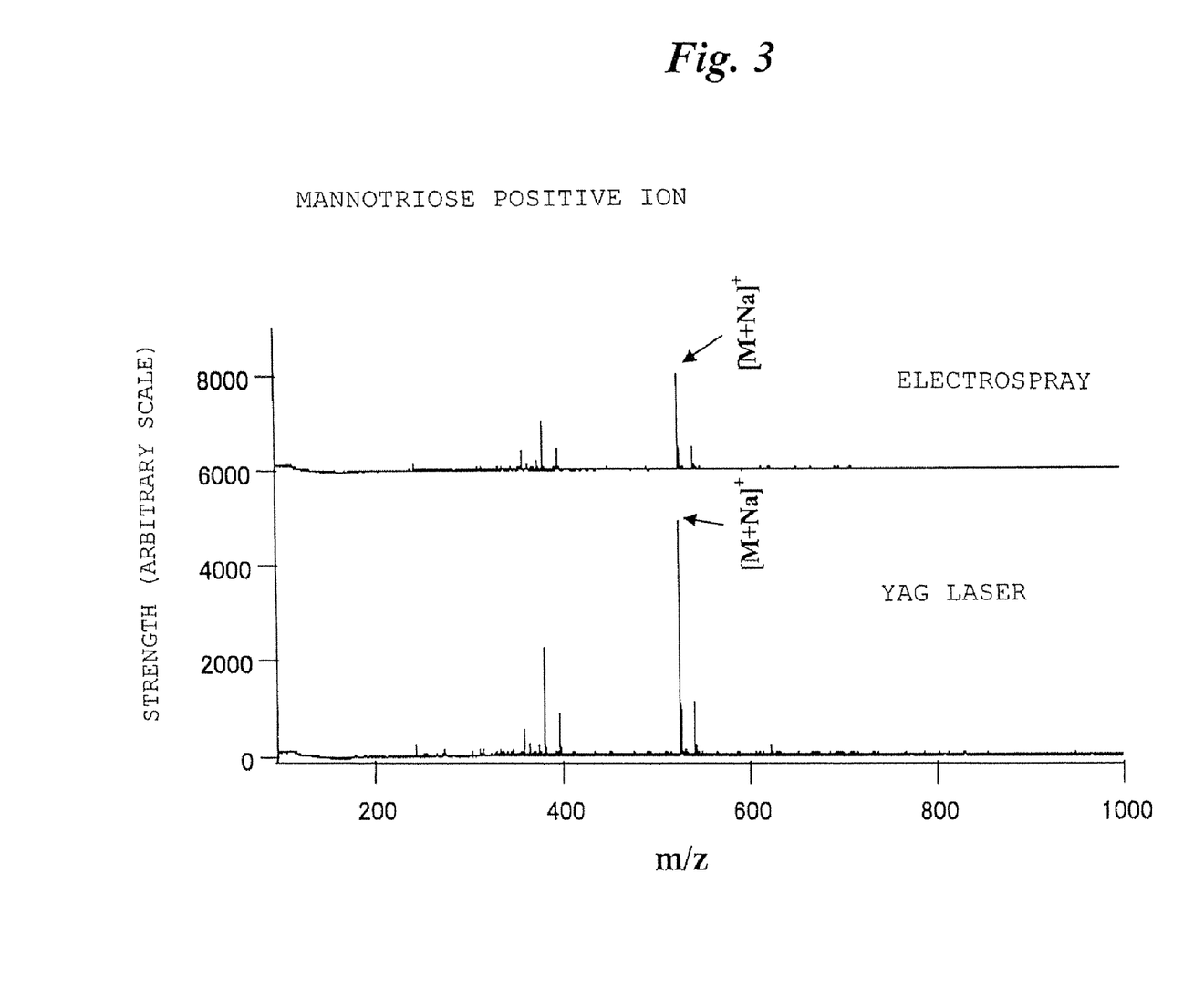
FIG. 3 illustrates an example of measurement of plasmon-assisted electrospray.

As an example of measurement using plasmon-assisted electrospray, FIG. 3 illustrates results of measuring an oligosaccharide by electrospray having an inner diameter of 30 μm and an outer diameter of 70 μm. It will be understood that the ion intensity of mannotriose, which is comparatively difficult to measure even with electrospray, is intensified greatly by irradiation with a 532-nm YAG laser beam. This result verifies the fact that desorption ionization efficiency with electrospray is greatly facilitated by plasmon excitation ascribable to the light intensifying electric field at the tip of a SUS capillary. The effect of this intensification has been observed similarly in proteins such as cytochrome c. Since the sample is taken up onto the surface of the needle tip at the molecular level with this plasmon-assisted electrospray method, further enhancement can be expected in the effect of intensifying desorption efficiency by plasmon assist.

As set forth above, the above-described ionization method has electrospray as its base and therefore biological macromolecules can be readily detected as multivalent ions. Further, in that it employs the sharp probe 10, this ionization method is an ultimate electrospray technique that can be extrapolated to electric-field desorption ionization regarded as the limit on electrospray. This means that a high ionization efficiency can be expected even in the presence of salt in a biological sample (under conditions of physiological saline).

Figure 4:
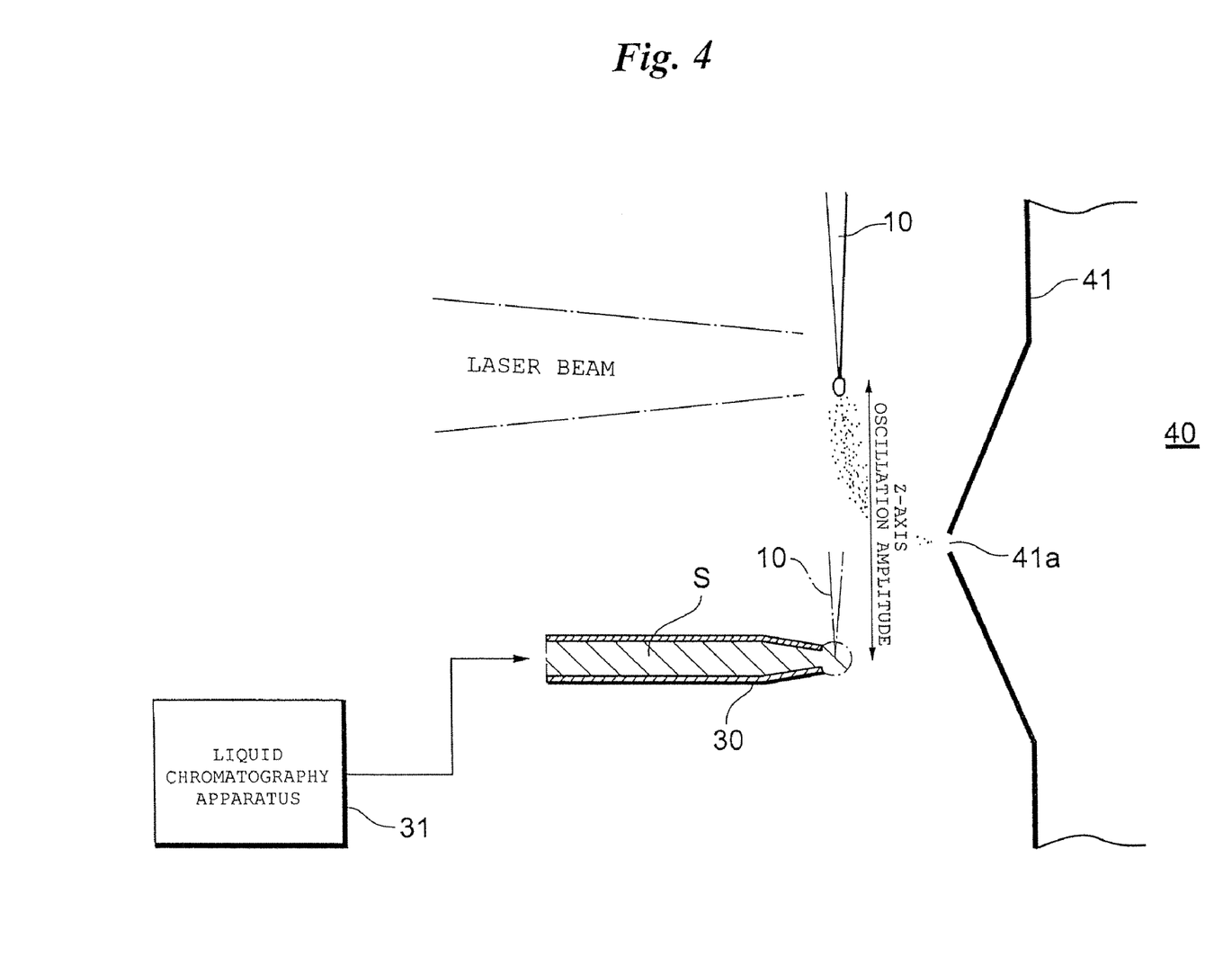
FIG. 4 illustrates the manner in which an ionization method according to a second embodiment is performed.

FIG. 4 illustrates a second embodiment. This embodiment has a configuration ideal for biological samples.

A high vacuum is maintained in a mass spectrometry apparatus 40. A portion of the mass spectrometry apparatus 40 into which ions are introduced is provided with a skimmer 41. The skimmer 41 has a very small hole (ion introduction port) 41a.

An electrospray capillary 30 is placed at the front face of the skimmer 41 of the mass spectrometry apparatus 40 (in a space at atmospheric pressure outside the mass spectrometry apparatus 40). The capillary 30 is connected to the outlet port of a liquid chromatography apparatus 31, and liquid that is output from the liquid chromatography apparatus 31 is supplied to the capillary 30.

The metal probe 10 is driven in oscillatory fashion between the position of a miniscule droplet produced at the tip of the capillary 30 (the sample capture position, bottom dead center, bottom end point or lower-limit position) and a position spaced slightly away (upward in the Figure) from this position (namely the origin position, top dead center, top end point or upper-limit position). The metal probe 10 is held by the Z-direction oscillating device in the same way as in the first embodiment and is driven in oscillatory fashion at, e.g., several hertz to several kilohertz along the longitudinal direction thereof (stages corresponding to the XY stage 13 and Z stage 12 are unnecessary in this embodiment). Oscillation may be a single reciprocation. Further, a positive or negative voltage on the order of several hundred to several thousand volts for generating electrospray is applied to the metal probe 10 (between the probe 10 and skimmer 41 of the mass spectrometry apparatus 40). An electrospray voltage (on the order of ±several hundred volts) may or may not be applied to the capillary 30 (between the capillary 30 and skimmer 41 of the mass spectrometry apparatus 40). (If the voltage is applied, the capillary 30 is made of metal.) In order to suppress the generation of electrospray between the probe 10 and capillary 30, the potential difference between them should be reduced (preferably the potentials are the same). The generation of electrospray takes place between the tip of the probe 10 and the ion-sampling skimmer (orifice) 41.

The tip of the probe 10 at the origin position is irradiated with an ultraviolet, visible or infrared laser beam from a laser unit. Components separated out by liquid chromatography are conveyed to the capillary 30. The probe (needle) 10 with the sharp tip is made to contact the liquid, which has flowed out from the tip of the capillary 30, from the side direction with respect to the axis of the capillary 30, thereby capturing the liquid sample. The probe 10 is oscillated up and down and produces the electrospray, and the biological sample, etc., is electrosprayed and subjected to mass spectrometry. The probe 10 is irradiated with an ultraviolet, visible or infrared laser beam to thereby promote the desorption of the sample. The generated ions are drawn into the vacuum chamber of the mass spectrometry apparatus 40 as a viscous stream from the side of atmospheric pressure.

Since a slender probe is used, clogging does not occur as it does in electrospray using the conventional capillary. Since the tip of the probe is sharp, electrospray is produced efficiently (the effect of the electric field is raised to the limit). The amount of sample taken up on the needle is increased by oscillating the probe at several to several tens of kilohertz. This leads to intensification of the ion signal.

If a probe having a tip diameter on the atomic level is used, then a nanometer level for the diameter of the probe tip can be achieved to the maximum degree. As a result, the electrospray phenomenon can be produced even for samples having a high salt concentration.

The liquid sample that emerges from the outlet port of the liquid chromatography apparatus is the object of measurement and combination with high-speed liquid chromatography is easy.

Figure 5:
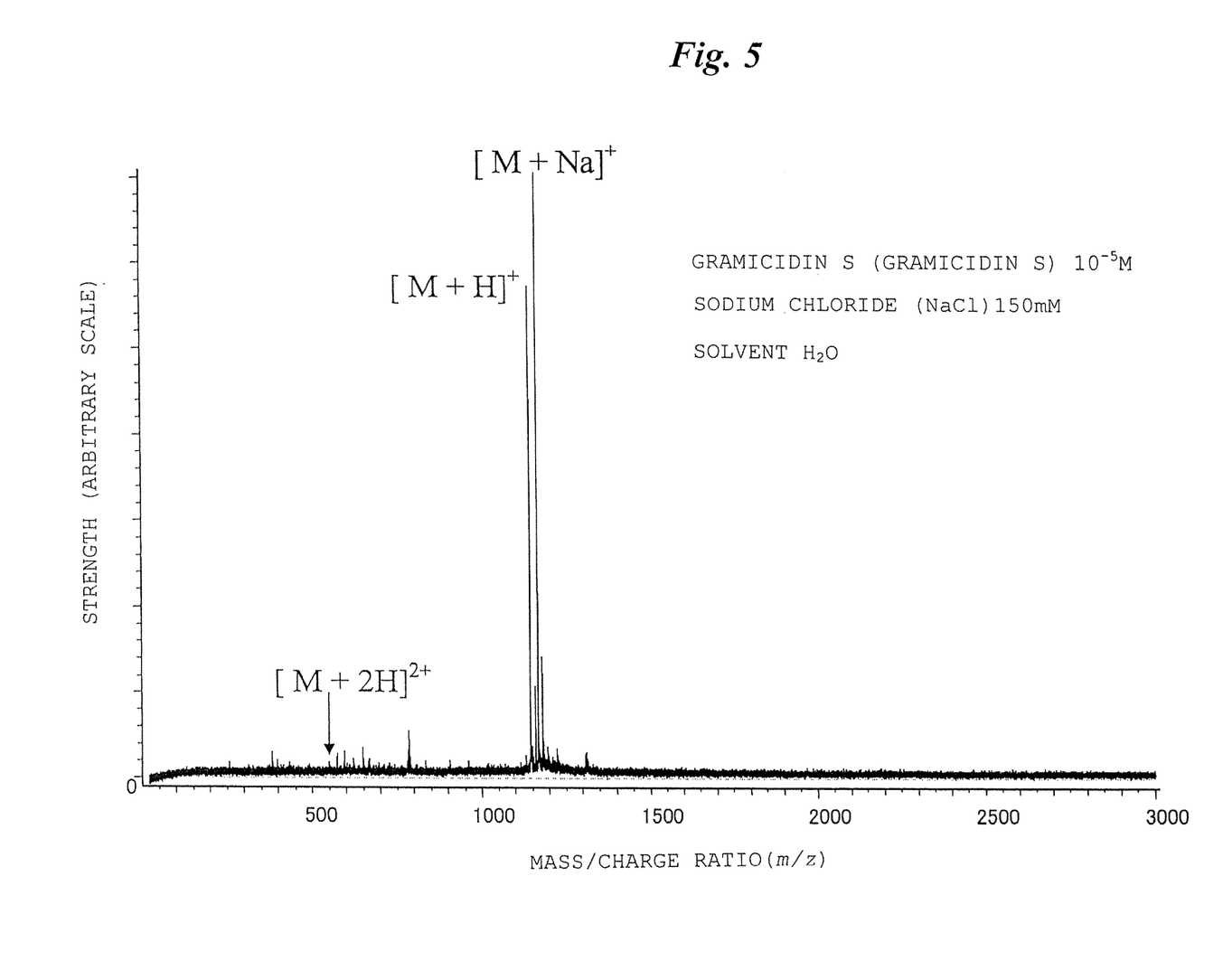
FIG. 5 is a diagram illustrating an example of analysis regarding a sample in which $10^{-5}$ M of gramicidin is dissolved in 150 mM of saline.

The capillary 30 need not be connected to the chromatography apparatus 31 and may be a simple slender tube for supplying the sample. FIG. 5 illustrates an example of results obtained by supplying a sample to such a slender tube for sample supply, subjecting the droplet formed at the tip of the tube to probe (needle) electrospray and analyzing the sample. Here $10^{-5}$M of gramicidin S dissolved in 150 mM of saline is adopted as the sample. With ordinary electrospray, it is difficult to spray a 150 mM saline droplet. However, as illustrated in FIG. 5, peptide ions are observed strongly under coexistence of 150 mM sodium chloride (NaCl). The liquid sample can be supplied upon being placed inside a vessel.

Stainless steel, platinum, gold, tungsten, platinum-indium alloy and silicon, etc., can be used as the probe material. If platinum or tungsten usable at high temperatures is employed, the probe will not be degraded by laser light (visible or infrared). Further, in a case where 532-nm visible laser light is used, for example, absorption of the 532-nm laser light is boosted as by coating the surface with gold.

Since a simple device such as a driving unit for producing reciprocating motion by utilizing magnetic drive or motor drive instead of piezoelectric element can be used as the Z-direction oscillatory driving device, the likelihood of widespread use at low cost is great.

In the first and second embodiments, voltage is applied to the probe in a variety of ways. Although voltage may be applied to the probe 10 continuously, it is preferred that in the process of bringing the tip of the probe 10 into contact with the biological sample S and capturing the sample, a high voltage not be applied to the probe 10 but that the high voltage be applied to the probe 10 at a position spaced sufficiently away from the sample surface to thereby produce the electrospray. That is, the biological sample is captured at the tip of the probe 10 (by the polarizing effect of the electric field) with the probe 10 and sample S being placed at the same potential or with the potential difference between them being made several volts to several tens of volts. (Positive and negative ions are captured selectively, with the probe 10 being placed at negative potential with respect to the biological sample in a case where positive ions are to be captured, and the reverse being performed in a case where negative ions are to be captured.) The probe 10 that has captured the sample at its tip leaves the biological sample S and reaches the top end point. A high voltage (several hundred to several thousand volts) is applied in pulsed form to the probe 10 at this position or in the vicinity thereof. The voltage of the probe 10 is returned to the original value at the moment the generation of electrospray ends. The sample captured at the tip of the probe 10 is desorbed (electrosprayed) from the probe 10 efficiently, in order to further heat and dry the charged droplet generated and in order to generate gaseous-phase ions efficiently from the droplet, the tip of the probe 10 is irradiated with infrared laser light (wavelength of 106 um) and 532-nm visible laser light (the laser may be either an infrared laser or a visible laser). This irradiation with laser light may be synchronized to the application of high voltage to the probe 10. If the vicinity of the probe tip is irradiated with infrared light, vaporization of the ions can be promoted by the rapid heating of the charged droplet.

Figure 6:
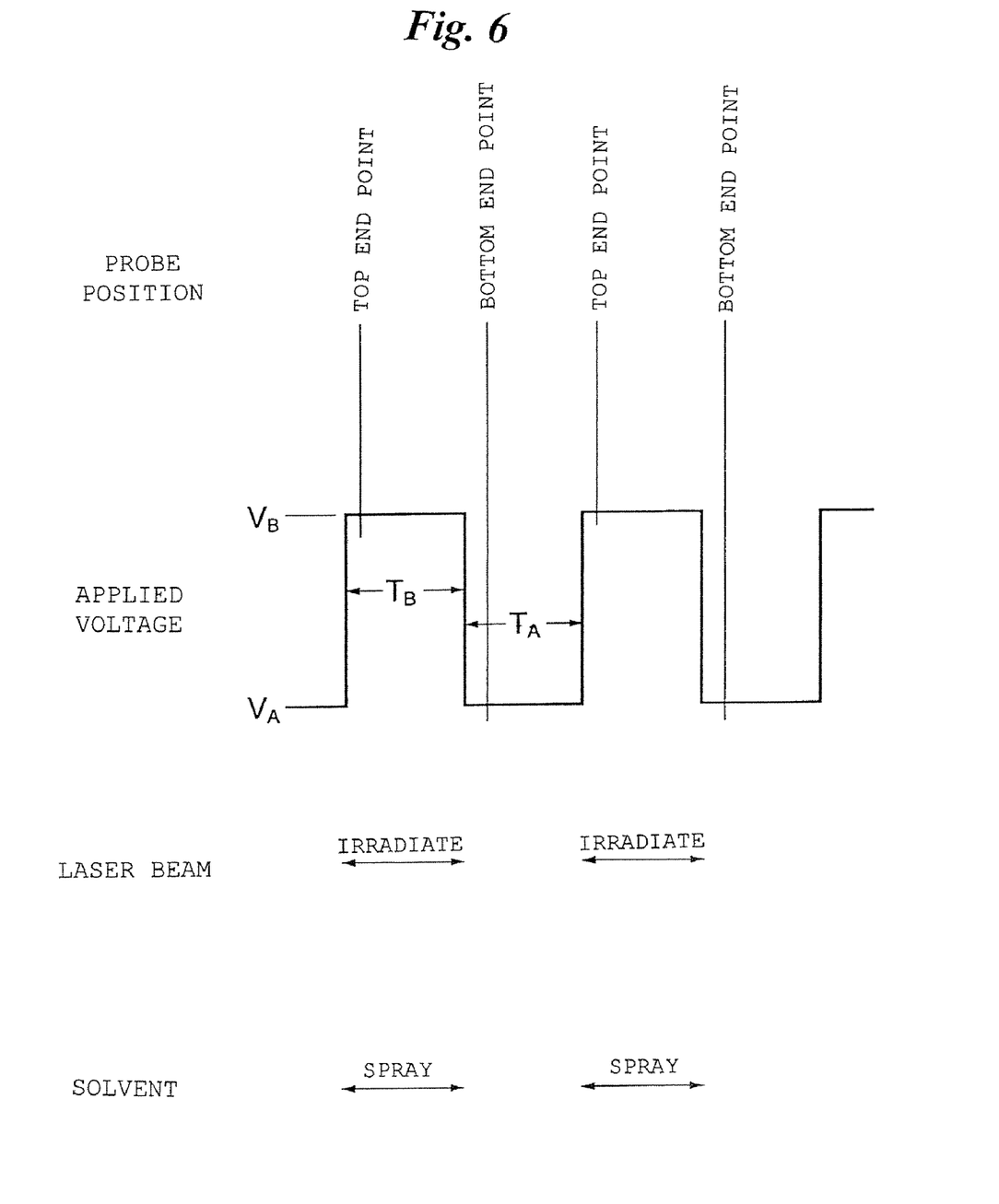
FIG. 6 is a chart illustrating timings of voltage application, laser beam irradiation and spraying of a solvent.

FIG. 6 is a timing chart representing the relationship among probe position, application of voltage to the probe and irradiation with the laser beam described above. The position at which the probe 10 farthest from the sample S is illustrated as the top end position, and the position at which the probe 10 is in contact with the sample S and penetrates to the greatest depth is illustrated as the bottom end point. The probe 10 is oscillated in reciprocating fashion (inclusive of a single reciprocation) between the top and bottom end points.

A pulsed voltage is generated by the power supply device 16 in synch with the oscillation of the probe 10 and the voltage is applied to the probe 10 [the pulsed voltage may be a rectangular waveform, as illustrated, a sinusoidal waveform obtained by smoothing the rectangular waveform slightly, a form obtained by slanting the top edge (to a rising slope or falling slope) of the rectangular wave, or a sawtooth waveform]. The voltage applied to the probe 10 attains the above-described high voltage (several hundred to several thousand volts) (let this voltage be a voltage $V_B$) immediately before the probe 10 arrives at the upper end point or in the vicinity of arrival. The high voltage is applied to the probe 10 while the probe 10 is in the vicinity of top dead center. The voltage applied to the probe 10 from the vicinity where the probe 10 is just about to reach the bottom end point (let this voltage be a voltage $V_A$) is made the same potential (0 V) as that of the sample S or several volts to several tens of volts relative to the sample.

Irradiation with laser light is performed in time period $T_B$ (a pulse width) during which high voltage is being applied to the probe 10. The duration of laser irradiation need not necessarily strictly agree with this time period $T_B$. The irradiation with the laser can be rendered intermittent by driving a mirror for reflecting the laser beam in synch with the change in applied voltage or the oscillation of the probe 10.

Preferably, it is arranged beforehand such that the values $V_A$, $V_B$ of the applied voltages, the time period $T_A$ during which the voltage $V_A$ is applied, the time period $T_B$ during which the voltage $V_B$ is applied and the waveform (at least one among these) can be adjusted appropriately in the power supply device 16 depending upon the type and properties of the sample S, whether laser irradiation is being performed or not or the wavelength thereof, as well as other conditions, in such a manner that ion detection sensitivity will be optimized.

There are cases where it is difficult to produce electrospray by the solvent being vaporized from the sample and the sample being dried while the sample S taken up on the probe 10 is moving upward (in the direction of the top end point). Further, there are cases where the sample of interest has a high component concentration, making it difficult to achieve the electrospray, as in the manner of a biological sample. In order to deal with such cases, it may be arranged to spray the biological sample with a solvent that readily produces electrospray, such as methanol, ethanol, acetonitrile, propanol or isopropanol (all of which are polar or non-polar solvents), thereby wetting the sample surface, diluting in the vicinity of the sample surface by the solvent and facilitating the occurrence of electrospray. It is preferred that the solvent be sprayed when the probe that has captured the sample has reached the vicinity of the top end point in synch with the irradiation with the laser beam, the application of voltage and the oscillation of the probe, as illustrated in FIG. 6.

Methods that can be adopted as methods of spraying the tip of the probe with solvent are (i) a method of continuously spraying a small amount of solvent toward the vicinity of the top end point of the probe, (ii) a method of spraying solvent mechanically at the instant the probe reaches the top end point (a solvent sprayer is oscillated laterally, etc.), and (iii) a method of firing a droplet dot toward the probe tip in a pulsed manner at the instant the probe reached the top end point, thereby wetting the tip with solvent.

A large number of modifications of the foregoing two embodiments can be mentioned in order to enlarge the amount of sample captured or to achieve three-dimensional imaging.

The surface area of the probe tip may be enlarged by cutting a groove such as threads into the probe tip (i.e., by forming unevenness), as mentioned above, in order to enlarge the amount of sample captured. Further, the probe may be rotated inside the sample (this is effective in three-dimensional imaging or in achieving uniform illumination by the laser light).

Furthermore, probe temperature may be controlled. For example, in case of a biological sample containing a large amount of water, the amount of sample that will be taken up on the probe is increased greatly if the probe is cooled to the vicinity of 0° C. or less. An increase in detection sensitivity is achieved as a result. Conversely, by raising probe temperature to room temperature or greater, a sample exhibiting little volatility (a highly viscous liquid, or a solid) can be fused and captured. By thus adjusting the temperature of the probe, capture at temperatures suited to various samples becomes possible and the range of application of the ionization method and apparatus of the present invention can be broadened. In order to control probe temperature, a temperature adjusting element such as a Peltier element may be provided on the probe or its holder.

In order to perform three-dimensional imaging, it is necessary to analyze molecules along the depth direction of the sample. The sample (e.g., a cell membrane) can be provided with a hole and the probe can be inserted into the sample through the hole, thereby enabling a deep portion of the sample beneath the sample surface to be captured as the object of measurement. Hole depth and depth of the sample captured can be controlled by adjusting the amplitude of oscillation of the probe. A probe whose tip has been cut to have threads may be used to pierce the sample. The portion of the sample incised can thus be kept to the minimum.

In a case where a cell is the sample of interest, often the biological sample is covered with a hard membrane. In such case it is difficult to sample the molecules within the biological sample with shallow piercing solely of the surface by the probe. There are also cases where it is necessary to image the molecules that exist inside a biological sample (at depth). In such cases the above-described sample capture method using piercing is ideal.

The method of rotating the probe in important in order to irradiate the surface of the probe with the laser beam uniformly.

Figure 7:
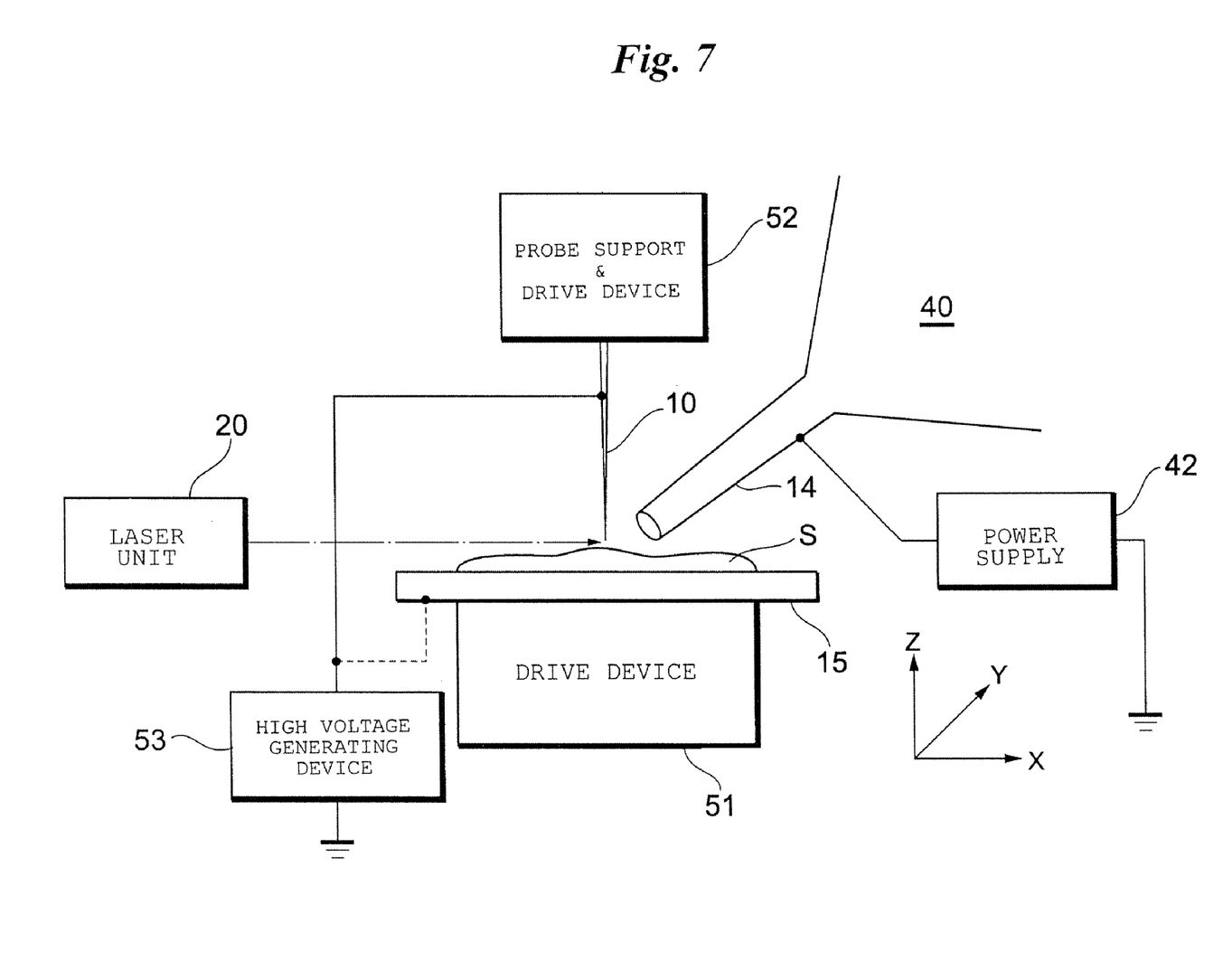
FIG. 7 illustrates the configuration of modification of the above embodiments.

FIG. 7 illustrates the configuration of an ionization apparatus and ionization analytical apparatus capable of imaging according to a modification of above embodiments.

The ionization apparatus comprises a support and drive device 52 of the probe 10, a sample table 15, a sample table drive device 51, a high voltage generating device 53 and the laser unit 20 and is capable of operating under atmospheric pressure as in the above embodiments. Sample ions desorbed and ionized from sample S by this ionization apparatus are introduced to a mass spectrometry apparatus 40. Although an orthogonal time-of-flight mass spectrometer can be mentioned as an example of the mass spectrometry apparatus, the present invention is also applicable to a mass spectrometry apparatus such as a (linear) ion-trapping mass spectrometry apparatus.

The ionization analytical apparatus comprises the ionization apparatus and the mass spectrometry apparatus 40. Some kinds of mass spectrometry apparatus include a power supply device 42 for supplying an ion focusing voltage (relatively low voltage less than +100V in a case of positive ion mode and less than −100V in a case of negative ion mode), the voltage being applied to an ion sampling capillary (orifice) 14. The ion sampling capillary 14 may be grounded in another type of mass spectrometry apparatus.

The probe (needle) 10 made of metal (or conductive material) is supported by the probe support and drive device 52 so as to be movable toward and away from the sample S placed on the sample table 15, perpendicularly or oblique to the surface of the table 15. The probe 10 is reciprocated (oscillated) in the longitudinal direction thereof by the device 52. It will suffice merely to reciprocate the probe once at one sampling point. The probe 10 is further moved along x, y directions (the same as X, Y directions) by the device 52. The sample table 15 is also supported by the device 51 so as to move along the X, Y and Z directions.

The ionization apparatus is provided with the laser unit 20 (e.g., a YAG laser) the laser emission direction of which is pointed toward the probe 10.

The tip of the ion-sampling capillary 14 is arranged so as to face the vicinity of the location where the tip of the probe 10 is provided. The capillary 14 is for introducing sample ions, which are generated at this location, to the mass spectrometry apparatus 40.

A direct high voltage of about several thousand volts for electrospray is applied, at all times (during measurement operation), between the ion-sampling capillary 14 and the probe 10 by the high voltage generating device 53 (and through the power supply device 42). A positive high voltage is applied to the probe 10 in a case of positive ion measurement mode, whereas a negative high voltage is applied in a case of negative ion measurement mode.

Preferably, the probe 10 and the sample table 15 (in a case of conductive) are wired so as to be the same potential (indicated by dot lines). The sample table 15 may be electrically floated, since the sample S is placed at the same potential when the probe 10 is brought into contact with the sample S.

The probe 10 is moved down and brought into contact with the sample S at a desired position thereof, preferably under a microscopy, thereby the sample is captured by the tip of the probe 10 (sampling). The probe 10 and the sample S are at the same potential while the probe 10 contacts the sample S. Then, the probe 10 is moved upward. At the moment when the probe 10 is separated from the sample S, an electrospray is produced at the tip of the probe by the potential difference applied between the probe 10 and the ion sampling capillary (nozzle, tube or orifice) 14 of the mass spectrometry apparatus 40, and molecules of the sample captured at the tip of the probe 10 are desorbed and ionized in the gaseous phase. The sample ions thus generated are drawn in by the capillary 14 and sent to the mass spectrometry apparatus 40.

A pulsed high voltage may be applied between the capillary 14 and the probe 10 after the probe 10 is separated away from the sample to produce an electrospray at the tip of the probe 10. In this case it is preferable to place the probe 10 and the sample at the same potential.

In this embodiment, the probe 10 and the sample S are always placed at the same potential, no electrospray toward the sample S from the probe 10 is produced. An electrospray toward the capillary 14 from the probe 10 is produced, at the moment when the probe 10 is separated from the sample S, by an electric field generated by the potential difference between the probe 10 and the capillary 14. In this case, the distance between the tip of the probe 10 and the tip of the capillary 14 may be close to less than several millimeters, so that ions generated by the electrospray are effectively introduced into the mass spectrometry apparatus 40. The maximum distance (displacement of the probe 10) between the probe 10 and the sample S can be less than 1 mm.

It is suffice to insert the probe 10 into the sample S once at one sampling position. Of course, the probe 10 is inserted into the sample S a plurality of times at one sampling position. Imaging is possible by changing the insert position of the probe 10.

In this modification, the probe 10 may also be irradiated by the laser unit 20 as in the above embodiments. Further it may be arranged to spray the sample with a solvent to facilitate the occurrence of electrospray as in the above embodiments.

Figure 8:
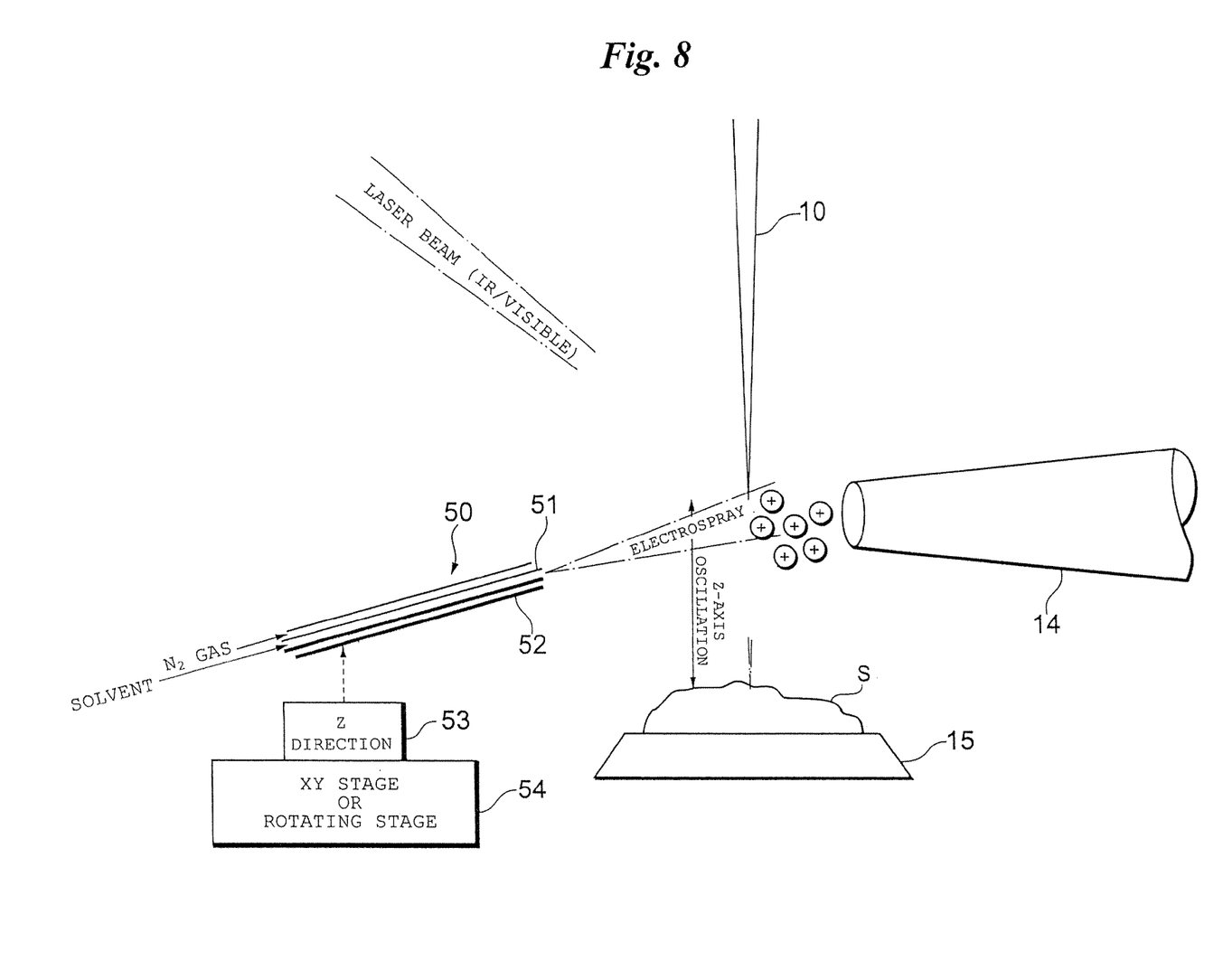
FIG. 8 illustrates the configuration of an ionization apparatus according to a third embodiment.

FIG. 8 illustrates a third embodiment. Items identical with those shown in the first and second embodiments set forth above are designated by like reference characters and are not described again.

The characterizing feature of the third embodiment includes placing a side electrospray apparatus 50 at a position diagonally below the origin position (top end point) of the probe and spraying a charged droplet (from diagonally downward position) from the electrospray apparatus (preferably a nanoelectrospray) 50 toward a trace amount of sample, which has been captured at the tip of the probe 10 located at the top end point, thereby dissolving and spraying the sample and blowing it through the ion-sampling capillary 14 so that it is introduced into the mass spectrometry apparatus. If the electrospray solvent is one such as water, ethanol, methanol or other electrolyte, any of these can be used.

The electrospray apparatus (nanoelectrospray apparatus) 50 includes a very slender metal capillary 51 supplied with solvent, and an external cylinder 52 provided outside the capillary with a clearance therebetween. A high voltage is applied to the capillary 51.

It may be so arranged that a pulsed high voltage (a pulsed voltage the same as the voltage applied to the probe shown in FIG. 6) is applied when the probe 10 reaches the top end point, or a fixed voltage may be applied at all times. A nebulizer gas [or assist gas (N2 gas, etc.)] is supplied into the space between the capillary 51 and external cylinder 52 as necessary, and the gas is jetted from the end thereof toward the probe 10.

The electrospray apparatus 50 is supported by an XY stage 54 and a Z stage 53 such that its position is freely adjustable in the XY directions and Z direction. A rotating stage can also be used instead of the XY stage. The electrospray apparatus 50 may be supported in such a manner that the inclination angle of the capillary 51 is freely adjustable. As the probe 10, use may be made of a needle-like slender wire, which has a nanometer-scale tip diameter, made of metal (gold, platinum, platinum-iridium alloy, tungsten, stainless steel, etc.) or of glass or quartz, which is an insulator (dielectric).

Unlike the first, second embodiments and modification thereof, it is not necessarily required to apply voltage to the probe 10 and therefore an insulator may be used for the probe 10.

The operation of the ionization apparatus in the third embodiment is as follows: The probe 10 is oscillated vertically (along the Z axis) so that a sample is captured at the tip of the probe 10 in a manner the same as in the first, second embodiments and modification thereof. At the position where the probe 10, which has captured the sample, has arrived at the top end point or the vicinity thereof, the tip of the probe 10 is exposed to a portion of the nanoelectric spray (near the outer periphery of the plume) produced at the side of the probe 10 by the electrospray apparatus 50. As a result, the sample that has been taken up at the tip of the probe 10 is desorbed and ionized. The function of the nanoelectrospray is to cause the sample at the tip of the probe 10 to be wetted and diluted by a charged droplet supplied by the nanoelectrospray. This facilitates the electrospraying of a sample having a high component concentration, such a sample being difficult to electrospray. Further, the desorption and ionization of the sample captured at the tip of the probe 10 can be promoted by pneumatic assist of the nanoelectrospray. The desorbed and ionized sample is introduced to the analyzing apparatus by the capillary 14.

In a case where metal is used as the probe 10, the potential of the probe 10 may be placed at the same potential as the sample at all times. In a case where the sample at the probe tip is not desorbed sufficiently by the side electrospray, a high voltage is applied in pulsed form to the probe 10, in a manner similar to that of the first and second embodiments, at the position where the tip of the probe 10 is exposed to a portion of the side electrospray plume, and the electrospray is generated forcibly at the tip of the probe 10 to thereby increase the strength of the ions.

It is possible to select side electrospray for two cases, namely a case where a nebulizer gas is used (pneumatic electrospray) and a case where this gas is not used. In a case where the nebulizer gas is not used, there is a possibility that the desorption of the sample captured at the probe tip will not be performed efficiently. A probe made of an insulator is used instead of a metal probe, therefore, thereby facilitating desorption of ions by coulomb repulsion. If the nebulizer gas is used, the sample at the probe tip is blown off by the air flow so that desorption is assisted. As a result, ion desorption and ionization are performed easily and more efficiently.

A high voltage can be applied in pulsed form to a metal probe and the sample at the probe tip can be electrosprayed to facilitate more efficient generation of ions. At the position where the probe 10 has reached the top end point, irradiation with a pulsed laser beam is performed in a manner similar to the case of the first, second embodiments and modification thereof, thereby facilitating heating of the liquid (infrared laser irradiation) or plasmon-excited desorption (only in the case of a metal probe, in which case irradiation with a 532-nm visible laser beam, for example, is preferred).

In the third embodiment as well, it goes without saying that it is possible to apply the modifications of the first and second embodiments, e.g., adjustment of probe temperature, rotation of the probe, formation of unevenness at the probe tip to enlarge surface area and piercing of the sample and insertion of the probe into the hole in order to realize three-dimensional imaging, etc.

What is claimed is:

1. An ionization method using electrospray, comprising:
oscillating a metal probe along the longitudinal direction thereof, with enough amplitude to bring the tip of the probe into contact with a sample, at an origin position where the tip of said probe is spaced away from the sample;
capturing the sample at the tip of said probe without applying a voltage to said probe at a position where the tip of said probe contacts the sample; and
subsequently applying a pulsed voltage, which is for producing electrospray, to said probe to thereby ionize the sample in a period of time during which the tip of said probe is in the vicinity of said origin position.

2. An ionization method according to claim 1, wherein the vicinity of the tip of said probe at said origin position is irradiated with a laser beam.

3. An ionization method according to claim 1, wherein a solvent is sprayed toward the vicinity of the tip of said probe at said origin position.

4. An ionization method according to claim 1, wherein the sample is supplied by placing it on a sample table.

5. An ionization method capable of imaging according to claim 1, further comprising moving said probe in a direction substantially along the sample surface while holding constant the distance between said probe tip and sample surface; obtaining an image of the sample surface conforming to the position of said probe; specifying a search area on this image; bringing said probe to the origin position within the search area; and oscillating said probe along the longitudinal direction thereof.

6. An ionization method according to claim 1, wherein a liquid sample is supplied from the tip of a capillary.

7. An ionization method according to claim 6, wherein a liquid sample is supplied to said capillary from liquid chromatography.

8. An analytical method for mass spectrometry of ions obtained by the ionization method set forth in claim 1.

9. An ionization method using electrospray, comprising:
holding a probe so as to be capable of reciprocating between a bottom end point at which a tip of the probe contacts a sample and a top end point at which the tip of the probe is spaced away from the sample;
arranging an ion guide introducing sample ions to a mass spectrometry apparatus such that the tip of the ion guide is positioned in the vicinity of the tip of the probe in the vicinity of the top end point;
moving the probe toward the bottom end point and bring the tip of the probe into contact with the sample to capture the sample;
causing the probe and the sample to be at the same potential at least during the probe contacts the sample; and
subsequently, moving the probe toward the top end point, and applying a high voltage for electrospray between the probe and the ion guide, at least at a time when the probe is separated from the sample, to thereby ionize the sample captured at the tip of the probe.

10. An ionization method according to claim 9, wherein the vicinity of the tip of the probe at the top end point is irradiated with a laser beam.

11. An ionization method according to claim 9, wherein a solvent is sprayed toward the vicinity of the tip of the probe at the top end point.

12. An ionization analytical method for mass spectrometry of ions generated by the ionization method set forth in claim 9 by introducing the generated sample ions to the mass spectrometry apparatus via the ion guide.

13. An ionization method using electrospray, comprising:
oscillating a probe along the longitudinal direction thereof, with enough amplitude to bring the tip of the probe into contact with a sample, at an origin position where the tip of said probe is spaced away from the sample, and capturing the sample at the tip of said probe without applying a voltage to said probe at a position where the tip of said probe contacts the sample; and
spraying a charged droplet from an electrospray apparatus toward the sample, which has been captured at the tip of said probe, in the vicinity of said origin position, thereby ionizing the sample.

14. An analytical method for mass spectrometry of ions obtained by the ionization method set forth in claim 13.

15. An ionization apparatus using electrospray, comprising:
sample holding means for holding a sample;
an oscillating device for oscillating a metal probe along the longitudinal direction thereof between an origin position where the tip of the probe is spaced away from the sample and a position where the tip of the probe contacts the sample; and
a power supply unit for generating a pulsed voltage for electrospray in synch with oscillation of said probe;
wherein no voltage is applied to said probe in a period of time during which the tip of said probe contacts the sample, and the pulsed voltage generated by said power supply unit is applied to said probe in a period of time during which the tip of said probe is in the vicinity of the origin position after the tip of said probe has contacted the sample and captured the sample.

16. An ionization apparatus according to claim 15, wherein said power supply unit generates a pulsed voltage applied to said probe, the pulsed voltage being such that at least one among amplitude, pulse width and pulse waveform can be varied.

17. An ionization apparatus using electrospray according to claim 15, further comprising a three-dimensional-displacement driving unit for moving at least one of the sample table and probe relatively toward and away from each other and translating the same, said apparatus being capable of imaging.

18. A mass spectrometry apparatus having the ionization apparatus set forth in claim 15.

19. An ionization apparatus comprising:
holding means for holding a probe so as to be capable of reciprocating between a bottom end point at which a tip of the probe contacts a sample and a top end point at which the tip of the probe is spaced away from the sample;
an ion guide, arranged such that the tip of the ion guide is positioned in the vicinity of the tip of the probe in the vicinity of the top end point, for introducing sample ions from the tip thereof to a mass spectrometry apparatus; and a high voltage generating apparatus applying a high voltage for electrospray between the probe and the ion guide, at least at a time when the probe is separated from the sample.

20. An ionization apparatus comprising:

sample holding means for holding a sample;

specimen capture means for oscillating a probe along the longitudinal direction thereof between an origin position where the tip of the probe is spaced away from the sample and a position where the tip of the probe contacts the sample, and capturing the sample without applying a voltage to said probe at a position where the tip of said probe contacts the sample; and an electrospray unit for forming an electrospray field at a position in the vicinity of the tip of the probe in the vicinity of said origin position, after the tip of said probe has contacted the sample and captured the sample.

* * * * *